United States Patent
Anzalone

(12) 
(10) Patent No.: US 6,288,241 B1
(45) Date of Patent: Sep. 11, 2001

(54) CRYSTALLINE POLYMORPHIC FORM OF 1-METHYL-5-P-TOLUOYLPYRRPLE-2-ACETAMIDOACETIC ACID GUAIACYL ESTER (MED 15)

(75) Inventor: Sergio Anzalone, Rome (IT)

(73) Assignee: Sigma-Tau Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/581,289
(22) PCT Filed: Dec. 16, 1998
(86) PCT No.: PCT/IT98/00363
§ 371 Date: Jun. 12, 2000
§ 102(e) Date: Jun. 12, 2000
(87) PCT Pub. No.: WO99/33797
PCT Pub. Date: Jul. 8, 1999

(30) Foreign Application Priority Data

Dec. 24, 1997 (IT) ............................................. RM97A0811

(51) Int. Cl.[7] .................. C07D 207/323; C07D 207/333; C07D 207/335
(52) U.S. Cl. ........................... 548/539; 548/561; 548/562
(58) Field of Search ................................... 548/539, 561, 548/562

(56) References Cited

U.S. PATENT DOCUMENTS 4,578,481  3/1986  Baglioni ................................ 548/539
4,882,349  11/1989  Baglioni ............................... 514/423

FOREIGN PATENT DOCUMENTS

| 0 088 734 A | 9/1983 | (EP) . |
| 0 134 763 A | 3/1985 | (EP) . |
| 0 755 679 A | 1/1997 | (EP) . |
| WO 99 07363 A | 2/1999 | (WO) . |

OTHER PUBLICATIONS

Tubaro et al, "Studies on the Gastric Tolerability of the New Non–Steroidal Anti–Inflammatory Drug Amtolmetin Guacyl" *Arzneimittel Forschung. Drug Research*, vol. 45, No. 12, Dec. 1995, pp. 1298–1302.

Caruso et al., "Pharmacological Properties and Toxicology of MED–15, a Prodrug of Tolmetin" *Drugs Under Experimental and Clinical Research*, vol. 18, No. 11/12, 1992, pp. 481–485.

Threlfall, Analysis of Organic Polymorphs, *Analyst*, vol. 120, Oct. 1995, pp. 2435–2460.

Giron, "Thermal Analysis and Calorimetric Methods in the Characterisation of Polymorphs and Solvates" *Thermochim.Acta*, vol. 24, 1995, pp. 1–59.

"Dialog Phind (Archival)", *Dialog Phind (Archival)*, Dec. 5, 1997, p. 9.

*Primary Examiner*—Jane C. Oswecki
(74) *Attorney, Agent, or Firm*—Nixon & Vanderhye

(57) ABSTRACT

A new crystalline form of 1-methyl-5-p-toluoylpyrrole-2-acetamidoacetic acid guaiacyl ester, a process for its preparation and pharmaceutical compositions endowed of antiinflammatory, analgesic and antipyretic activity containing same are disclosed.

2 Claims, No Drawings

CRYSTALLINE POLYMORPHIC FORM OF 1-METHYL-5-P-TOLUOYLPYRRPLE-2-ACETAMIDOACETIC ACID GUAIACYL ESTER (MED 15)

This application is a 371 of PCT/IT98/00363 filed Dec. 16, 1998.

The present invention relates to a new crystalline form of 1-methyl-5-p-toluoylpyrrole-2-acetamidoacetic acid guaiacyl ester, a process for its preparation and to pharmaceutical compositions endowed with antiinflammatory, analgesic and antipyretic activity containing same.

The ester of 1-methyl-5-p-toluoylpyrrole-2-acetamidoacetic acid (hereinafter referred to as MED 15, form 1) is a known compound.

In fact, U.S. Pat. No. 4,882,349 discloses a class of N-mono-substituted and N,N-disubstituted amides of 1-methyl-5-p-toluoylpyrrole-2-acetic acid (known as Tolmetin) endowed of anti-inflammatory, analgesic, antipyretic, antisecretive and antitussive properties.

U.S. Pat. No. 4,578,481 claims a specific compound, endowed with valuable pharmacological activity, encompassed in the above-mentioned class, precisely 1-methyl-5-p-toluoylpyrrole-2-acetamido-acetic acid guaiacyl ester (which is MED 15, form 1), and a process for its preparation.

The process disclosed in U.S. Pat. No. 4,578,481 presents some drawbacks, since it is not easily applicable on industrial scale and gives low yields.

According to the above-mentioned process, Tolmetin was reacted with N,N'-carbonyldiimidazole in tetrahydrofuran (THF), and aminoacetic acid ethyl ester hydrochloride was added to the reaction mixture.

Following a complex series of washings in order to remove the unreacted starting compounds, and crystallisation from benzene/cyclohexane, 1-methyl-5-p-toluoylpyrrole-2-acetamidoacetic acid ethyl ester was obtained. This compound was subsequently transformed into the corresponding acid.

The acid was reacted with N,N'-carbonyldiimidazole obtaining the corresponding imidazolide, to which a solution of guaiacol in THF was added.

From the reaction mixture, following several washings, neutralisation and crystallisation from benzene/cyclohexane MED 15 form 1 was obtained.

The main physico-chemical characteristics of MED 15 form 1 are shown in table 1, left column.

There are various known possibilities for the administration of any drug, thus this may be conveniently done per oral route, using suitable pharmaceutical formulations such as tablets, sugar-coated pills and capsules, or per rectal route using, for example, suppositories.

These administrations way present obvious advantages in comparison with the parenteral route (injectable route) because they do not need the presence of a physician or a person able to use a syringe.

Good manufacturing practices of the above-mentioned pharmaceutical formulations, suitable for an oral administration, request that several parameters, depending on the nature of the drug, be respected.

Non-limiting examples of such parameters are: stability of the drug utilised as starting materials in different environment conditions; stability during the production process; and stability of the final pharmaceutical formulations.

The drug utilised for the preparation of the above mentioned pharmaceutical formulations must be as pure as possible, and its stability during prolonged storage periods in different environment conditions must be controlled, avoiding the use of degraded drug, or drug having unexpectedly lower titre than the one requested by the production process. In such case the content of the drug present in a single sugar-coated pill or capsule would be undesirably lower than wanted.

The absorption of humidity decreases the drug titre because of the increase of the drug weight, which is due to its capacity to absorb water.

For this reason drugs which tend to absorb humidity must be protected during long term storage, for example using suitable dehydrating agents, or storing them in an environment protected from humidity.

Humidity may decrease drug titre also during the production process when the drug is exposed in normal conditions to humidity, without any protection.

The correct distribution of an exact amount, in weight, of drug in single sugar-coated pills or capsules is a critical factor, particularly when low drug dosages are utilised.

It is possible to reduce the dimension of drug particles to a suitable value, for example by milling, in order to obtain a correct distribution of a drug.

In fact, small particles are better distributed in constant amount, in single sugar-coated pills or capsules.

Since milling may provoke a certain degree of drug degradation, high stability to milling represents an important advantage for the preparation of capsules or sugar-coated pills containing the due amount of drug, avoiding the presence of degradation products.

Moreover, during milling, mechanical stress on the solid product may provoke polymorphic alteration, amorphization, and alteration of the crystalline shape or surface.

These alterations play a fundamental role in the subsequent technological process to which the product is undertaken and on the bio-pharmaceutical characteristics.

The stability of the active principle contained in the pharmaceutical composition is essential for determining the time of drug validity. In this period the drug can be administered without any risk, either due to the presence of an excessive quantity of potentially dangerous degradation products, or to low content of the active ingredient, lower than the established amount.

The stability of the drug in different storage conditions represents supplemental advantages both for patients and for the manufacturer; in fact, storage in controlled environment and frequent substitution of expired batches are avoided.

Any modification of the solid state of the orally administered drug, such as capsules, tablets or sugar-coated pills, which improves its physical and chemical stability, and gives rise to a significant advantage in comparison with less stable form of the same drug, would be a very desirable goal.

It is well known that a significant example of the above mentioned modifications includes a new crystalline form of the drug, which overcomes the above-mentioned drawbacks.

It is an object of the present invention to provide a new crystalline form of MED 15 (in the following as MED 15, form 2) which does not present the above-mentioned drawbacks.

A further scope of the present invention is to provide a process, which overcomes the drawbacks of the known methods. This process is industrially applicable with high yield and is suitable for preparing MED 15, form 2 with high degree of purity.

It has now been found that 1-methyl-5-p-toluoylpyrrole-2-acetamidoacetic acid guaiacyl ester of formula

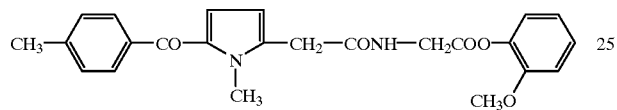

presents the polymorphism phenomenon and in addition to the above-mentioned MED 15, form 1, it also exists in a second crystalline form, designated as MED 15, form 2, characterised by the following physico-chemical characteristics:

melting point: 133–136° C.;

DSC

| Peak | 136.2° C. | 136.7° C. |
|---|---|---|
| Onset | 132.5° C. | 133.7° C. |
| Delta H | 97.3 J/g | 98.3 J/g |

IR spectrum (presenting characteristic signals at the following wave numbers in cm$^{-1}$)

| 3302.98 | 1550.27 | 1113.95 | 699.06 |
|---|---|---|---|
| 3092.37 | 1501.85 | 1037.43 | 620.38 |
| 2948.24 | 1480.85 | 1022.34 | 576.81 cm$^{-1}$ |
| 2842.00 | 1458.18 | 976.95 | |
| 1785.85 | 1377.94 | 885.21 | |
| 1762.26 | 1310.86 | 833.34 | |
| 1646.73 | 1262.66 | 788.30 | |
| 1626.80 | 1202.46 | 769.16 | |
| 1607.82 | 1179.67 | 749.21 | |
| 1564.93 | 1162.83 | 729.28 | |

Some fundamental physico-chemical characteristic values (melting point, differential scanning calorimetry, DSC, and I.R. spectrum) are shown, for comparison purposes, in Table 1. These values show the difference between the two forms.

TABLE 1

Comparison between the physico-chemical characteristics (melting point, DSC, IR spectrum) of MED 15, form 1, and form 2.

| | MED 15, form 1 | | | | MED 15, form 2 | | | |
|---|---|---|---|---|---|---|---|---|
| Melting point* | 117–120° C. | | | | 132–136° C. | | | |
| DSC** | | | | | | | | |
| Peak | 129.5–130.9° C. | | | | 136.2–136.7° C. | | | |
| Onset | 125.4–125.9° C. | | | | 132.5–133.7° C. | | | |
| Delta H | 97.7–101.1 J/g | | | | 97.3–98.3 J/g | | | |
| IR Spectrum*** | 3315.47 | 1486.29 | 968.53 | 636.42 | 3302.98 | 1550.27 | 1113.95 | 699.06 |
| (wave numbers in cm$^{-1}$) | 3296.85 | 1455.29 | 936.82 | 621.99 | 3092.37 | 1501.85 | 1037.43 | 620.38 |
| | 3066.96 | 1408.70 | 918.44 | 556.44 | 2948.24 | 1480.85 | 1022.34 | 576.81 |
| | 2931.05 | 1375.95 | 882.01 | | 2842.00 | 1458.18 | 976.95 | |
| | 2841.60 | 1312.38 | 838.68 | | 1785.85 | 1377.94 | 885.21 | |
| | 1775.59 | 1261.40 | 786.11 | | 1762.26 | 1310.86 | 833.34 | |
| | 1690.25 | 1195.71 | 771.47 | | 1646.73 | 1262.66 | 788.30 | |
| | 1608.54 | 1149.65 | 748.46 | | 1626.80 | 1202.46 | 769.16 | |
| | 1549.69 | 1110.65 | 740.19 | | 1607.82 | 1179.67 | 749.21 | |
| | 1501.99 | 1032.86 | 687.71 | | 1564.93 | 1162.83 | 729.28 | |

*Measured by Capillar Buchi Apparatus.
**Apparatus: DSC Mettler 30; temperature: from 50 to 200° C.; scanning speed 10° C./min; amount weighed: from 3 to 8 mg.
***FTIR spectrophotometry Apparatus: Nicolet Mod. 20SXC; form of the sample: tablet; concentration of the sample: 2% on KBr; temperature: room temperature.

The process according to the invention is shown in the following reaction scheme:

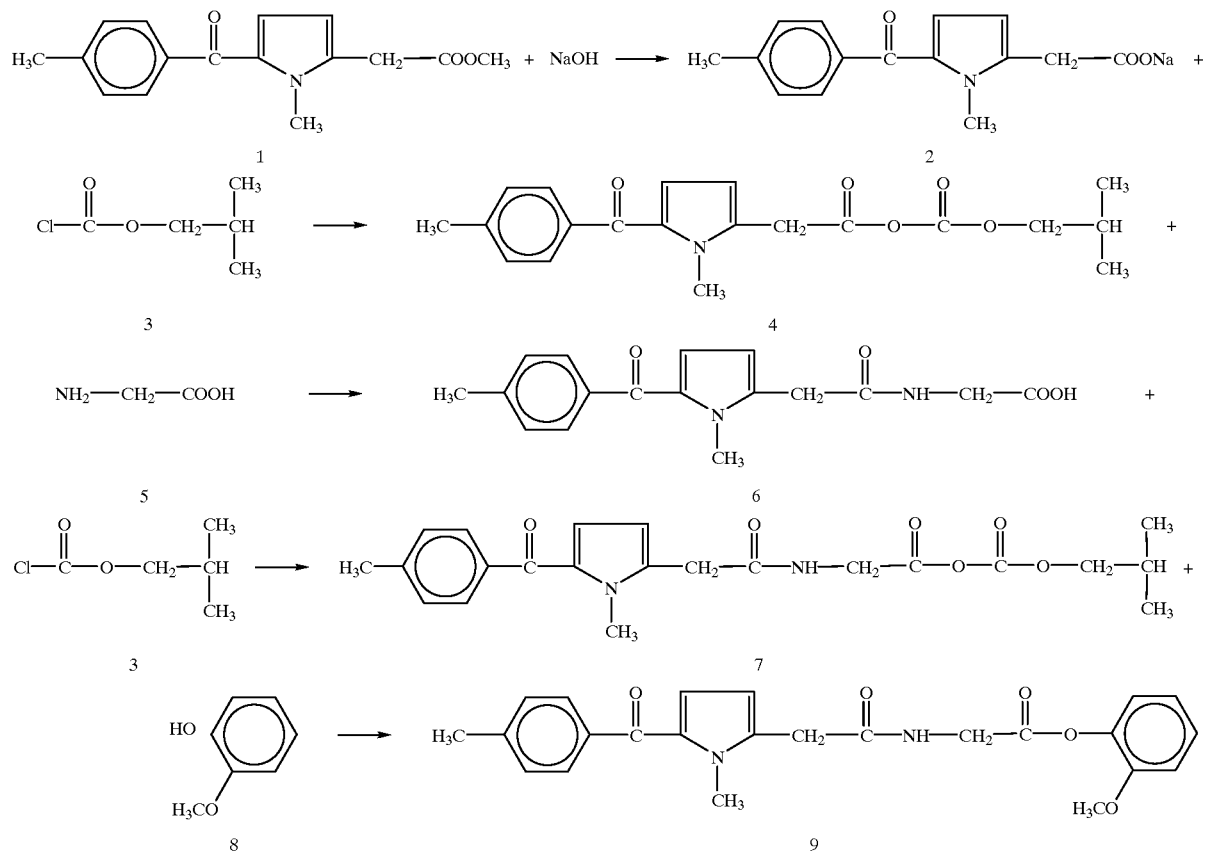

The above mentioned process comprises the following steps:

(a) hydrolysing TOLMETIN 1 methyl ester with an alkaline hydroxide in a basic environment, obtaining TOLMETIN 2 alkaline salt;

(b) condensing 2 with isobutylchloroformate 3 obtaining the mixed anhydride 4;

(c) reacting 4 with glycine 5 obtaining 1-methyl-5-p-toluoylpyrrol-2-acetoamidacetic acid 6;

(d) condensing 6 with isobutylchloroformate 3 obtaining the mixed anhydride 7; and (e) reacting the mixed anhydride 7 with guaiacol 8 obtaining 9, MED 15, form 2.

The following non-limiting example illustrates the preparation of MED 15, form 2, according to the process of the present invention.

Preparation of 1-methyl-p-toluoylpirrol-2-acetoammidoacetic acid.

A mixture of 500 mL of toluene, 100 g of Tolmetin ethyl ester and 10 g of Terre deco in IL flask, was heated to 70° C. and maintained at this temperature for 20–30 min, under stirring. The mixture was then filtered on pre-heated buckner, and the solid phase washed with 50 mL of heated toluene. The discoloured toluene solution was transferred in a 2 L flask, 15 g of sodium hydroxide (97%) dissolved in 100 mL of water were added thereto.

The solution was heated at reflux temperature and refluxed for 1 hour. 22 mL of isobutyl alcohol were added to the solution which was heated at reflux temperature; water (about 120 mL) was removed completely with Marcusson's apparatus arriving up to 104–105° C. inner temperature.

To a suspension of Tolmetin sodium, cooled under nitrogen atmosphere to −5° C.±2° C., 0.2 mL of N-methyl Morpholine were added. Maintaining the temperature at 0° C.±3° C., 53 mL of isobutyl chloroformate were added dropwise in 5–10 min. After about 1 hour the suspension became fluid. Following 3 hours of reaction at 0° C.±3° C., over the glycine solution previously prepared, the mixed anhydride solution was added dropwise. The glycine solution was prepared in a flask containing 230 mL of demineralised water, 47 g of potassium hydrate (90%), cooling the solution to 20° C.±2, adding 60 g of glycine, and again cooling to 10° C.±2° C.

To the glycine solution, the mixed anhydride was added dropwise under stirring, in 5–10 min., maintaining the temperature at 20° C.±2° C.

At the end of the addition, temperature was left to rise to room temperature, 1 hour later the reaction was complete. To the mixture 325 mL of demineralised water were added, the mixture was brought to pH 6.0±2 using diluted (16%) hydrochloric acid (about 100 mL).

The temperature of the solution was brought to 73° C.±2° C. and the pH adjusted to pH 5.0±0.2.

The separation of the two phases was made at hot temperature: the toluene phase was set aside for recovering acid-Tolmetin if any, the water phase was maintained at 73° C.±2° C. and brought to pH 4.0±0.2 using diluted hydrochloric acid.

At the beginning of the precipitation the solution was slowly brought to pH 3.0±0.2 using diluted (16%) hydrochloric acid (100 mL).

The mixture was cooled to 15° C.±3° C. and after 30 min. filtered. The solid cake was washed with 2×100 mL of demineralised water, the product was dried at 60° C. under vacuum till constant weight. 100 g of 1-methyl-p-toluoylpirrol-2-acetoammidoacetic acid were obtained.

Preparation of MED 15, Form 2

To a 2 L flask containing 730 mL of toluene, 100 g of dried compound of the above step were dissolved. To this solution 18.8 g of potassium hydrate (tit. 90%) in 65 mL of water were added.

The solution was dried maintaining the internal temperature at 95–100° C., and cooled to 55–60° C. A solution of potassium hydrogen carbonate was then added and the resulting mixture was dried maintaining the internal temperature at 105° C.±2° C.

The mixture was cooled under nitrogen atmosphere to 5° C.±2° C., 24 mL of isobutyl alcohol and 0.3 mL of N-methyl morpholine were added thereto.

Maintaining the temperature at 10° C.±3° C., 47 mL of isobutyl-chloroformate were added dropwise in 5–10 minutes. The mixture was left to react for two hours at 10° C.±3° C. obtaining an anhydride solution, which was added to a guaiacol solution previously prepared.

The guaiacol solution was prepared by loading in a 2L-flask 295 mL of water, 25 g of potassium hydrate (90%), and 0.3 g of sodium metabisulfite.

At the end of the loading the temperature was brought to 35–40° C.

The anhydride was added dropwise in 5–10 min and the temperature was left to rise to room temperature.

The suspension was kept under stirring for 1 hour and brought to pH 6.0±0.5 with diluted hydrochloric acid. The suspension was heated to 70° C.±5° C. and maintained at pH 3–4 with diluted hydrochloric acid.

The phases were separated while hot. The aqueous phase was discharged, and to the organic phase, 250 mL of water were added.

Maintaining the temperature at 70±5° C. the solution was brought to pH 8.0±0.5 with diluted sodium hydrate, the phases were separated while hot and the acqueous phase was discharged.

The organic phase was washed with 250 mL of water. At 70±5° C. the phases were separated. The toluene phase was then cleared with dicalite, filtered and left to crystallise.

The mixture was slowly cooled to 30° C.–35° C., the temperature was then brought to 10±3° C. and after 1 hour filtered, washed with toluene (2×100 mL).

The product was brought to dryness at 60° C. under vacuum, thus giving 100 g of compound MED 15, form 2. Theoretical yield: 133.7 g; Yield %: 74.8%.

What is claimed is:

1. 1-Methyl-5-p-toluoylpyrrole-2-acetamidoacetic acid guaiacyl ester form 2, having formula

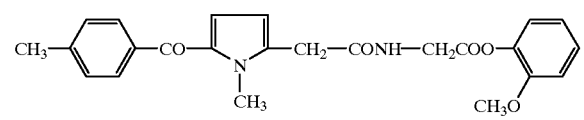

characterised by the following physico-chemical characteristics:

melting point: 133–136° C.;
DSC

| Peak | 136.2° C. | 136.7° C. |
| Onset | 132.5° C. | 133.7° C. |
| Delta H | 97.3 J/g | 98.3 J/g |

IR spectrum (presenting characteristic signals at the following wave numbers in cm$^{-1}$)

| | | | |
|---|---|---|---|
| 3302.98 | 1550.27 | 1113.95 | 699.06 |
| 3092.37 | 1501.85 | 1037.43 | 620.38 |
| 2948.24 | 1480.85 | 1022.34 | 576.81 cm$^{-1}$ |
| 2842.00 | 1458.18 | 976.95 | |
| 1785.85 | 1377.94 | 885.21 | |
| 1762.26 | 1310.86 | 833.34 | |
| 1646.73 | 1262.66 | 788.30 | |
| 1626.80 | 1202.46 | 769.16 | |
| 1607.82 | 1179.67 | 749.21 | |
| 1564.93 | 1162.83 | 729.28 | |

2. A process for preparing the compound of claim 1, according to the following reaction scheme:

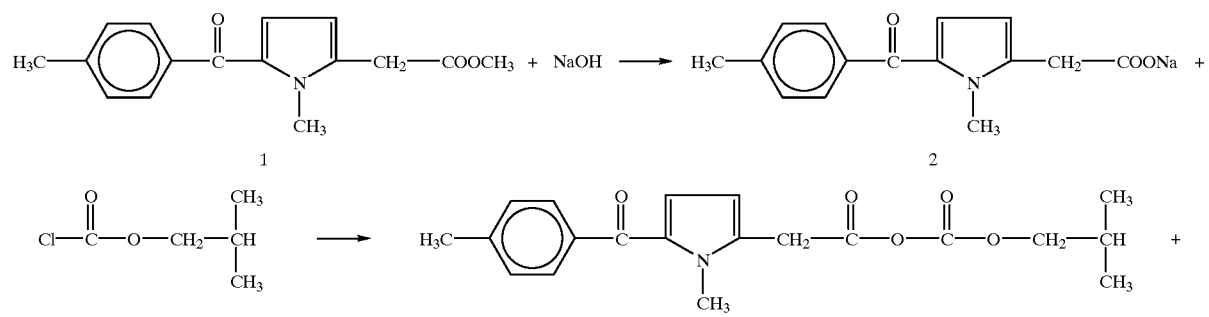

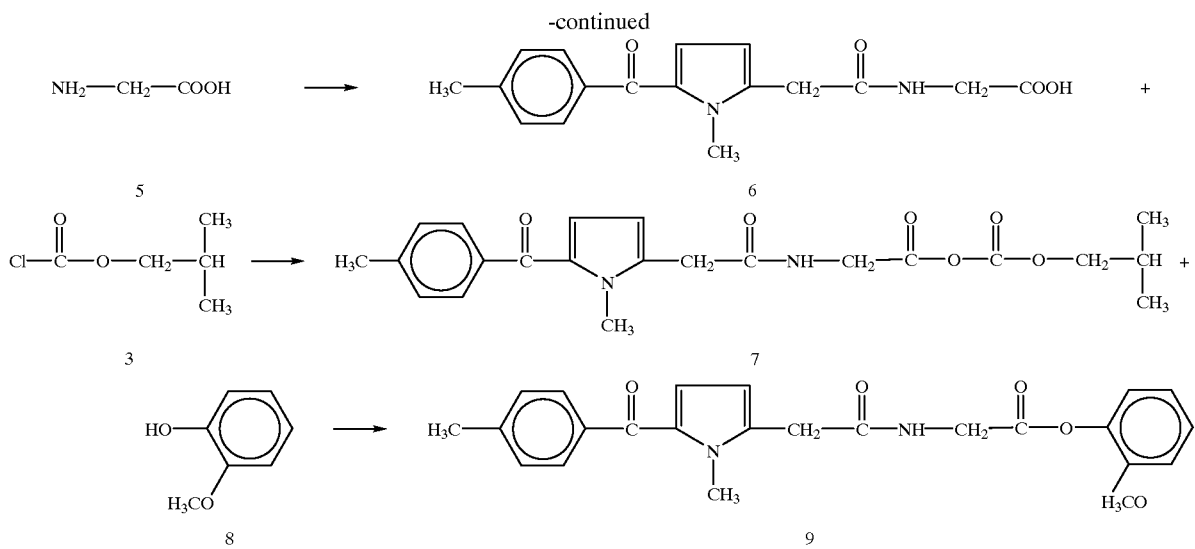

which comprises the following steps:
(a) hydrolising Tolemetin 1 methyl ester with an alkaline hydroxide in a basic environment, to obtain Tolmetin 2 alkaline salt;
(b) condensing Tolmetin 2 with isobutylchloroformate 3 to obtain the mixed anhydride 4;
(c) reacting mixed anhydride 4 with glycine 5 to obtain 1-methyl-5-p-toluoyl-pyrrol-2-acetoamidacetic acid 6;
(d) condensing 1-methyl-5-p-toluoyl-pyrrol-2-acetoamidacetic acid 6 with isobutylchloroformate 3 to obtain the mixed anhydride 7; and
(e) reacting the mixed anhydride 7 with guaiacol 8 to obtain 9 1-methyl-5-p-toluoylpyrrole-2-acetamidoacetic acid guaiacyl ester, form 2.

* * * * *

UNITED STATES PATENT AND TRADEMARK OFFICE
CERTIFICATE OF CORRECTION

PATENT NO.    : 6,288,241 B1
DATED         : September 11, 2001
INVENTOR(S)   : Anzalone It is certified that error appears in the above-identified patent and that said Letters Patent is hereby corrected as shown below:

Title page,
Item [73], Assignee, should read as follows;

[73] Assignee Sigma-Tau Industrie Farmaceutiche Riuntie S.p.A. and Medosan Industrie Biochimiche Riunite srl.

Signed and Sealed this

Twenty-seventh Day of November, 2001

*Attest:*

*Attesting Officer*

NICHOLAS P. GODICI
*Acting Director of the United States Patent and Trademark Office*